(12) United States Patent
Kabir et al.

(10) Patent No.: US 8,399,261 B2
(45) Date of Patent: Mar. 19, 2013

(54) LATERAL FLOW ASSAY SYSTEM AND METHODS FOR ITS USE

(75) Inventors: Mazbahul Kabir, Seattle, WA (US); Syamal Raychaudhuri, Seattle, WA (US); James William Needham, Seattle, WA (US); Stanislaw Morkowski, Seattle, WA (US)

(73) Assignee: Inbios International, Inc., Seattle, WA (US)

( * ) Notice: Subject to any disclaimer, the term of this patent is extended or adjusted under 35 U.S.C. 154(b) by 420 days.

(21) Appl. No.: 12/666,637

(22) PCT Filed: Jun. 27, 2008

(86) PCT No.: PCT/US2008/068621
§ 371 (c)(1),
(2), (4) Date: Dec. 23, 2009

(87) PCT Pub. No.: WO2009/003177
PCT Pub. Date: Dec. 31, 2008

(65) Prior Publication Data
US 2010/0330585 A1     Dec. 30, 2010

Related U.S. Application Data

(60) Provisional application No. 60/946,678, filed on Jun. 27, 2007.

(51) Int. Cl.
*G01N 33/558* (2006.01)
*G01N 33/553* (2006.01)

(52) U.S. Cl. ........ 436/514; 422/420; 422/421; 422/424; 422/425; 422/426; 422/427; 422/429; 422/430; 435/7.1; 435/7.93; 435/7.94; 435/7.95; 435/969; 435/970; 436/518; 436/524; 436/808; 436/810

(58) Field of Classification Search .............. 422/420, 422/421, 424, 425, 426, 427, 429, 430; 436/514, 436/518, 808, 810, 525; 435/7.1, 7.93, 7.94, 435/7.95, 969, 970
See application file for complete search history.

(56) References Cited

U.S. PATENT DOCUMENTS

| | | | |
|---|---|---|---|
| 4,313,734 A | | 2/1982 | Leuvering |
| 4,444,879 A | * | 4/1984 | Foster et al. ............... 435/7.95 |
| 4,943,522 A | * | 7/1990 | Eisinger et al. ............ 435/7.25 |
| 6,485,982 B1 | | 11/2002 | Charlton |
| 6,663,833 B1 | | 12/2003 | Stave et al. |
| 6,841,159 B2 | | 1/2005 | Simonson |
| 7,090,803 B1 | | 8/2006 | Gould et al. |
| 7,144,742 B2 | | 12/2006 | Boehringer et al. |
| 2006/0008921 A1 | | 1/2006 | Daniels et al. |
| 2006/0275922 A1 | | 12/2006 | Gould et al. |
| 2007/0020768 A1 | | 1/2007 | Rundstrom et al. |

FOREIGN PATENT DOCUMENTS

| | | |
|---|---|---|
| WO | 2007055712 A1 | 5/2007 |
| WO | 2007056114 A2 | 5/2007 |

OTHER PUBLICATIONS

ICN Flow product catalog, 1991-1992, pp. 597-599.*
Egger, Denise et al., "Colloidal Gold Staining and Immunoprobing of Proteins on the Same Nitrocellulose Blot," Analytical Biochemistry vol. 166, pp. 413-417 (1987).

* cited by examiner

*Primary Examiner* — Chris L Chin
(74) *Attorney, Agent, or Firm* — Speckman Law Group PLLC; Janet Sleath

(57) ABSTRACT

A lateral flow test system together with methods for its use in the detection of one or more analytes, or components, of interest within a sample, such as a biological sample, is provided. The system comprises a liquid formulation of a gold conjugate and a lateral flow assay device that does not include a conjugate pad having conjugate dried thereon.

16 Claims, 5 Drawing Sheets

LATERAL FLOW ASSAY SYSTEM AND METHODS FOR ITS USE

REFERENCE TO RELATED APPLICATIONS

This application is the US national phase entry of International Patent Application No. PCT/US2008/068621, filed Jun. 27, 2008, which claims priority to U.S. Provisional Patent Application No. 60/946,678, filed Jun. 27, 2007.

FIELD OF THE INVENTION

The present invention relates generally to methods and systems for assaying an analyte, such as a ligand, within a fluid sample. More specifically, the invention relates to methods that employ lateral flow devices and indicator particles to determine the presence and/or amount of a ligand in a biological sample.

BACKGROUND OF THE INVENTION

Immunochromatographic assays, also called lateral flow tests or simply strip tests, have been used for some time. They are a logical extension of the technology used in latex agglutination tests, the first of which was developed in 1956 by Singer and Plotz (Am. J. Med. 1956 21(6):888-92). The benefits of immunochromatographic tests include: (a) they have a user-friendly format; (b) a very short time is required to obtain the test result; (c) they have long-term stability over a wide range of climates; and (d) they are relatively inexpensive to make. These features make strip tests ideal for applications such as home testing, rapid point-of-care testing, and testing in the field for various environmental and agricultural analytes. In addition, they provide reliable testing that might not otherwise be available in developing countries.

Lateral flow assays can be used to detect any ligand that can be bound to a visually detectable solid support, such as dyed microspheres, both qualitatively and, in many cases, semi-quantitatively. Some of the more common lateral flow tests currently on the market are those for pregnancy, strep throat and *Chlamydia* infection. For these conditions a quantitative assay is not necessary.

In general, lateral flow immunoassays are simple one- or two-step assays for the qualitative determination of analytes directly in patient samples. A rapid lateral flow test consists of a system of overlapping porous materials containing the dried components needed to perform the test. These membranes are assembled in small strips, which may be placed into a plastic housing for ease in handling.

A typical lateral flow assay format is shown in FIG. 1. The sample to be tested, such as biological sample, is loaded onto sample application pad 10. In the case of whole blood or capillary blood samples, separation of blood cells and plasma takes place on sample pad 10. The liquid fraction of the sample then moves through a conjugate release pad 12 onto which a conjugate has been dried. The conjugate consists of detection molecules specifically directed against the analyte of interest and indicator particles, such as colloidal gold or gold sol. Upon contact with the liquid sample, the conjugate redissolves and specifically binds to any analyte present in the sample to form an analyte-conjugate complex.

This complex flows through a nitrocellulose membrane 14, also referred to as the analytical membrane, on which test and control reagents have been immobilized. More specifically, membrane 14 is provided with two capture lines, or regions, arranged sequentially and positioned perpendicularly to the flow direction, each containing bound reagents. Test line 16 contains analyte-specific molecules which are able to bind to and immobilize the analyte-conjugate complex, resulting in a visible colored line. Control line 18 does not contain analyte-specific molecules but is able to fix non-bound conjugate-containing particles. The formation of a colored line at control line 18 indicates that the test sample has flowed past test line 16. The color intensity observed at test line 16 is directly proportional to the analyte concentration in the sample and therefore enables semi-quantitative interpretation of the test result. If the analyte of interest is present at a level above the detection limit, test line 16 and control line 18 both become clearly visible. If the analyte is present at a level below the detection limit, only control line 18 becomes visible during the test.

The last component of the rapid test device is an absorbent pad 20 (also known as a wicking or sink pad) which collects the fluid flowing through the test system and prevents any backflow of fluid. Absorbent pad 20 allows the use of samples whose volume exceeds the wicking capacity of nitrocellulose membrane 14.

Many lateral flow assays in use today employ dehydrated antibody-gold sol conjugates as a visible indicator as described, for example, in U.S. Pat. No. 6,485,982. However, it is known that gold conjugates loose a significant amount of potency and sensitivity during the drying process, even if a number of stabilizers are employed in the process.

Gold conjugates in solution have long been used in another type of immunodiagnostic assay system called a "flow through" device, wherein layers of membranes and absorbent papers are stacked on top of each other. In this system, samples and reagents are applied in sequence and liquid flows vertically through the device. For example, US published Patent Application No. US 2005/0124077 A1 describes a vertical 'flow through' assay and apparatus which requires pre-incubation of test sample with indicator conjugate (e.g. typically an antibody bound to colloidal gold). No conjugate pad is needed. A number of difficulties are intrinsic to a flow through system, including the need for a plastic housing that is capable of allowing the incorporation of layers of papers on top of each other. In addition, the process is prone to clogging which necessitates that samples be processed very carefully, and/or extra steps/filters be added so that only clean samples go through the membrane layer. The use of an aqueous sol dispersion of a metal, such as gold, as a visible indicator is known in the art and is disclosed, for example, in U.S. Pat. No. 4,313,734.

U.S. Pat. No. 7,090,803 B1 and US published Patent Application No. 2006/0275922 A1 provide a device and method for lateral flow immunoassay where a pre-incubation of sample and liquid conjugated indicator (e.g. liquid conjugated gold) precedes lateral flow on a test strip, leading to better sensitivity. No conjugate pad is needed, however a separate mixing time period between the sample and the conjugated indicator is needed.

There remains a need in the art for a lateral flow assay system with high specificity and sensitivity, that is both easy to use and stable under a variety of environmental conditions, and that gives a result in a short amount of time.

SUMMARY OF THE INVENTION

The present invention provides a lateral flow test system together with methods for its use in the detection of one or more analytes of interest within a sample, such as a biological sample. The system disclosed herein may be employed to detect the presence of an analyte that is indicative of a disorder or condition such as infectious diseases, pregnancy, microbial infections, cancer, autoimmune disorders, cardiac disorders, allergic disorders, drug abuse, and the like. Analytes that may be detected using the disclosed system and methods include, but are not limited to, proteins and/or peptides, including ligands and receptors; non-protein molecules, such as carbohydrates, phospholipids, and nucleic acids; small molecules; and other molecules of biological interest.

Unlike many lateral flow assays currently available, the system disclosed herein does not require a conjugate pad having a conjugate, such as a gold conjugate, dried and immobilized on the pad. Thus, the system is less expensive to manufacture. Instead, a liquid formulation of a conjugated indicator, such as gold conjugate, is applied to the lateral flow test device following application of a test sample and a chase buffer. A second application of chase buffer is made following application of the liquid gold conjugate. The absence of a separate pad comprising a dried gold conjugate also simplifies manufacture of the device, leading to further reduced costs. The disclosed system and methods employ a lateral flow system and thus have the known advantages of lateral flow systems. Similar to U.S. Pat. No. 7,090,803, the disclosed assay system uses liquid conjugate indicator but is more straight-forward and easier to use, involves fewer steps and still achieves high sensitivity. No premixing or pre-incubation is needed between the test sample and liquid indicator conjugate. In addition, as detailed below, the system disclosed herein provides superior results compared to conventional lateral assay devices that employ a conjugate pad.

In one aspect, a system for detecting the presence of an analyte, or component, of interest in a sample, preferably a biological sample, is provided, wherein the system comprises a lateral flow assay device and a liquid formulation of a conjugated indicator, such as gold conjugate. The lateral flow assay device comprises: (a) a sample receiving region; and (b) a capture membrane including a test region comprising an immobilized detection agent specific for the analyte, and a control region including an immobilized reagent that binds to the detection agent. The lateral flow assay device may also include a reservoir region positioned downstream of the capture membrane for absorbing excess fluid, such as excess of the biological sample, liquid formulation of a conjugated indicator or an excess of a chase buffer that may be used with the assay device as further described below.

In another aspect, a lateral flow assay device for detecting the presence of an analyte of interest in a test sample is provided, the device consisting essentially of: (a) a sample receiving region; (b) a capture membrane comprising a test region including an immobilized detection agent specific for the analyte of interest and a control region positioned downstream of the test region and including an immobilized reagent that binds to the detection agent; and (c) a reservoir region positioned downstream of the capture membrane for absorbing excess fluid.

In a related aspect, kits for the detection of an analyte, or component, are provided, such kits comprising a lateral flow assay device disclosed herein, and a container of a liquid gold conjugate formulation, packaged together with instructions for using the device and liquid gold conjugate to detect the presence of the analyte in a sample, such as a biological sample.

In a further aspect, methods for detecting the presence of an analyte of interest in a liquid test sample are provided. In certain embodiments, such methods comprise: (a) providing a lateral flow assay device described herein; (b) applying the test sample to the sample receiving region; (c) applying a first volume of a chase buffer to the sample receiving region; (d) applying a liquid formulation of a gold conjugate to the sample receiving region to form an analyte-gold conjugate complex; (e) applying a second volume of a chase buffer to the sample receiving region; and (f) allowing the analyte-gold conjugate complex to migrate through the capture membrane to the test region and contact the detection agent thereby immobilizing the analyte-gold conjugate complex and forming a detectable signal, wherein formation of the signal indicates the presence of the analyte in the sample.

The above-mentioned and additional features of the present invention and the manner of obtaining them shall become apparent, and the invention shall be best understood by reference to the following more detailed description. All references disclosed herein are hereby incorporated by reference in their entirety as if each was incorporated individually.

DETAILED DESCRIPTION OF THE INVENTION

The present invention provides systems and methods for detecting the presence of an analyte in a sample, preferably a biological sample. As used herein, the term "analyte" encompasses proteins and/or peptides, including ligands and receptors; non-protein molecules, such as carbohydrates, phospholipids and nucleic acid molecules; small molecules; and other molecules of biological interest. Examples of samples that may be tested using the disclosed systems and methods include, but are not limited to, whole blood, serum, plasma, nasal secretions, sputum, urine, saliva, transdermal exudates, cerebrospinal fluid, and vaginal or urethral secretions. Fecal samples can also be tested following suitable processing.

Figure 2:
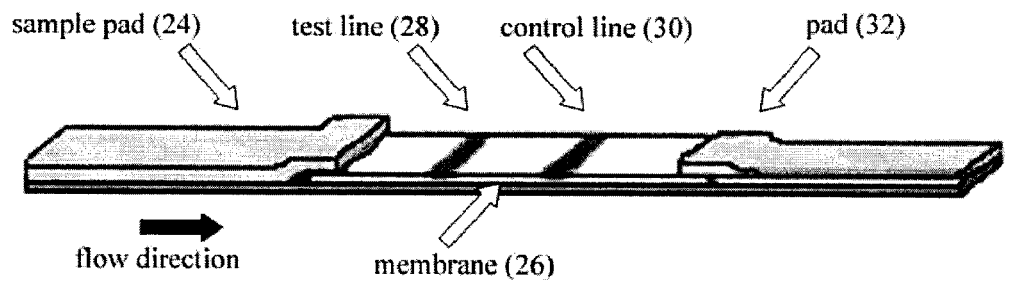
FIG. 2 shows a lateral flow assay device for use in the disclosed systems and methods.

One embodiment of a lateral flow assay device 22 for use in the disclosed methods and systems is shown in FIG. 2. Device 22 comprises a sample pad 24 onto which can be placed a liquid test sample suspected of containing an analyte. Sample pad 24, which is used to buffer test samples for optimal reaction with a liquid indicator conjugate (such as liquid gold conjugate) and then with a immobilized detection agent as detailed below, comprises a layer of support material that is capable of serving as a template for conjugate and sample application. In addition, sample pad 24 may include at least one layer of material that aids in providing consistent liquid flow, wetting, buffering and pH maintenance of fluids, and/or aids in biological sample separation. For serum and plasma based assays, a single layer of material that helps with consistent liquid flow, buffering, wetting and step wise mixing process may be used. For assaying blood samples, sample pad 24 may additionally include materials that can separate blood cells. Examples of appropriate materials are well known in the art.

Fluid flows from sample pad 24 laterally to, and downstream to, capture membrane 26 which is provided with a test line 28 and a control line 30. Membrane 26 may be formed of materials generally employed in lateral flow test devices and well known to those of skill in the art, such as nitrocellulose. Following application of test line 28 and control line 30, membrane 26 may be laminated with a series of synthetic and/or natural paper products of appropriate sizes and porosities.

While test line 28 and control line 30 are illustrated as being positioned serially along the flow path, those of skill in the art shall appreciate that other configurations of test and control sites may be employed. Test line 28 comprises at least one detection agent immobilized on membrane 26 that is specific for the analyte of interest. Detection agents that may be effectively employed in the disclosed device are well known to those of skill in the art and include antigens, antibodies, nucleic acid molecules, and other relevant protein or non-protein molecules. For example, the detection agent may comprise an antibody that specifically binds to a known disease antigen. Multiple test lines may be employed depending on the number of analyte-specific detection agents to be incorporated, and/or to enable testing for more than one analyte.

Control line 30, which is used as an internal control to ensure that all the test components are working, comprises molecules that bind to the detection agent irrespective of the presence or absence of the analyte. For example, for antigen-antibody interactions, control line 30 may comprise anti-Protein A or human IgG immobilized on membrane 26. An absorbent pad 32 is provided at, or in proximity to, the end of the flow path. Pad 32 absorbs any excess fluid and prevents any backflow of fluid towards sample pad 24.

In use, the liquid test sample is applied onto sample pad 24, followed by a first application of a buffer (referred to as the chase buffer), a predetermined amount of a liquid formulation of a gold conjugate, and lastly a second application of either the same or a different chase buffer to facilitate the flow of the gold conjugate upwards. The chase buffer employed varies depending on the analyte to be detected. A typical chase buffer contains a salt, detergent, protein solution and preservative, and has a pH in the range of 6 and 10, for example between 7 and 8. In some cases, other or fewer components are employed in the chase buffer as required to achieve the desired specificity and sensitivity.

In general, the gold conjugate comprises a first member of a binding pair that binds to a second member of the binding pair, and also to a component commonly present within the test sample, whereby the test sample forms a complex with the gold conjugate. The second member of the binding pair is immobilized at control line 30. The gold conjugate may have the same composition as gold conjugates commonly used in a dried form in conventional lateral flow assay devices. For example, protein A (PA) or protein G (PG) are commonly employed as the first member of the binding pair, with anti-PA or anti-PG antibodies being used as the second member of the binding pair. The amount and concentration of liquid gold conjugate added to the sample pad shall vary depending on the analyte to be detected Gold conjugate is readily made by following published protocols (see, for example, Bioconjugate Techniques; Chapter 14, pp 593-604; Greg T Hermanson; Academic Press). The gold conjugate is formulated in a buffer (pH range between 6 and 10) containing stabilizer such as detergent, sugar, protein solutions and/or other relevant blocking components. The gold conjugate is preferably stable for at least one year.

The chase buffer aids in the movement of any complex formed between the gold conjugate and the analyte laterally along the device. The volume of chase buffer shall vary depending on the system, and may be between 5-500 µl, for example between 10-100 µl. In certain embodiments, the chase buffer comprises a buffer system such as phosphate, Tris-Cl borate, bicarbonate, etc, mixed with a detergent such as Tween 20, Triton X-100 or other non-ionic detergent, CHAPS, non interfering protein blocking substances, such as bovine serum albumin, gelatin or other animal serum- or milk-derived proteins, such as casein, and anti-microbial and anti-fungal substances, such as sodium azides. Considering the needs for product shelf life and ease of evaluation, phosphate based buffers may be preferred.

The gold-labeled test sample then moves laterally upward through the device until it reaches test line 28, where any analyte present within the sample-gold complex binds to the detection reagent and becomes immobilized, resulting in a detectable colored line at test line 28. Unbound complex continues to travel upwards and will bind to, and be immobilized at, control line 30 resulting in a detectable colored line. If a colored line is not observed at control line 30, the test is considered invalid.

While the specific embodiment described above employs a colloidal particle system as the detection system, it shall be appreciated that the detection system used in the assay system disclosed herein can be any particulate and/or non-particulate system that is capable of generating signals that can be detected visually and/or with the aid of instrumentation. In addition, a fluidics system may be employed that enables the whole process to be automated and easily controlled.

The following Examples are offered by way of illustration and not by way of limitation.

EXAMPLES

Studies were performed to compare the effectiveness of the disclosed lateral flow assay system in detecting infectious diseases with that of a conventional lateral flow assay device. These studies employed dilution panels of sera confirmed positive for Chagas disease (*Trypanosome cruzi*), Visceral Leishmaniasis (Kala-azar) or Syphilis. A number of confirmed negative sera were used as controls. The ELISA reactivity of these panels was also established to facilitate setting a cut-off.

Figure 1:
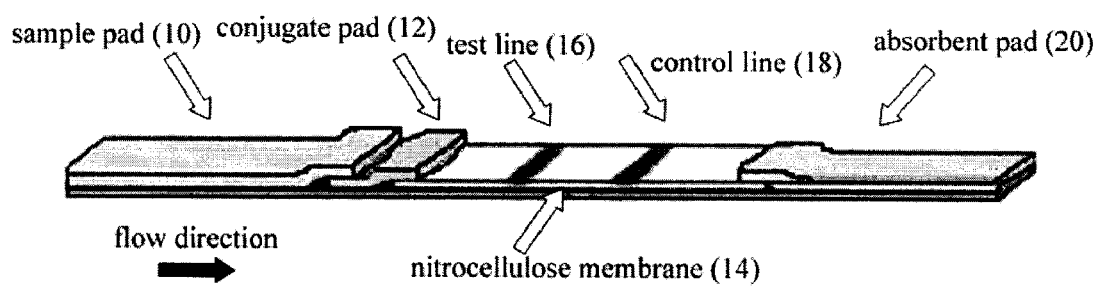
FIG. 1 shows a typical prior art lateral flow assay device.

Rapid assay systems were assembled as shown in FIGS. 1 and 2, and described above. The studies described below used the protein A and G gold system, with chicken anti-protein A being used as the control line. A conjugate of gold and either Protein A (PA) or Protein G (PG) was used either as a colloidal suspension, or dried onto a glass fiber pad (referred to as the conjugate pad) prior to lamination with a nitrocellulose membrane. Sample pads were soaked in an appropriate buffer and dried prior to laminating with or without the gold conjugate pad. Test and control lines were striped (1 µl/cm) on the nitrocellulose membrane using an automated BioJet system (BioDot Inc, Irvine, Calif.) prior to lamination.

A variety of nitrocellulose membranes from a number of sources were evaluated. The membranes were screened based on their pore size, flow rate, and consistency in obtaining reproducible results. Nitrocellulose membrane Hi-Flow™ Plus, manufactured by Millipore Corporation was then chosen for the experiments outlined below. Phosphate based chase buffer at pH 7.4 was employed for the studies described below, however a number of other buffers in the pH range between 6.5 and 10.0 can be used.

The concentration of antigens in phosphate buffer employed in the studies was varied between 0.025 mg/ml and 1 mg/ml. Those of skill in the art shall appreciate that the concentration of antigen can be adjusted as necessary to achieve needed sensitivity. For the experiments described below, the concentration of antigen was kept at 50 ug/ml in phosphate buffer, pH 7.4.

Example 1

Detection of Visceral Leishmaniasis (Kala-Azar) Infection

The well studied recombinant k39 antigen system (Zijlstra et al. *Clin. Diag. Lab. Immunol.* 5:717-720, 1998) was used to study the ability of the disclosed system to detect the presence of visceral leishmaniasis (also known as Kala-Azar) infection. The antigen was applied at concentrations between 0.025 mg/ml and 1 mg/ml to form a test line, with chicken anti-Protein A being used as the control line. For the conventional system, a conjugate pad with dried gold was used at high concentration that was optimized and selected earlier (Sundar S et al., *Jnl. Clin. Microbiol.* 44:251, 2006). For the modified system, gold concentration was varied between 0.5 and 5 optical units (measured at 525 nm) in a small volume (1 drop, or 10-20 μl). The volume and OD can be adjusted depending on the system to achieve desired specificity and sensitivity. Performance of the assay was examined using a k39 reactive serum dilution panel, which was prepared by mixing k39 reactive patients' serum with pooled normal sera.

Figure 3A:
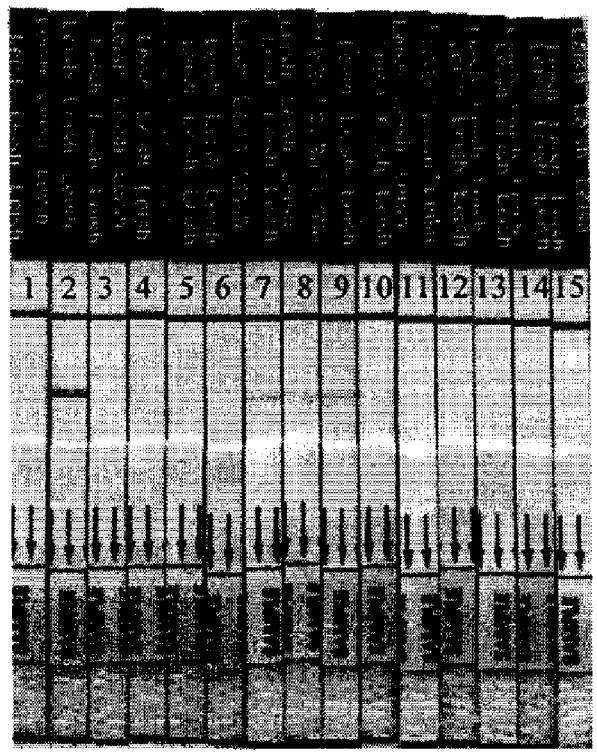
FIGS. 3A and B shows the detection of antibodies to recombinant k39 antigen in sera using a conventional lateral flow system (FIG. 3A) and the modified lateral flow system disclosed herein (FIG. 3B).
Figure 3B:
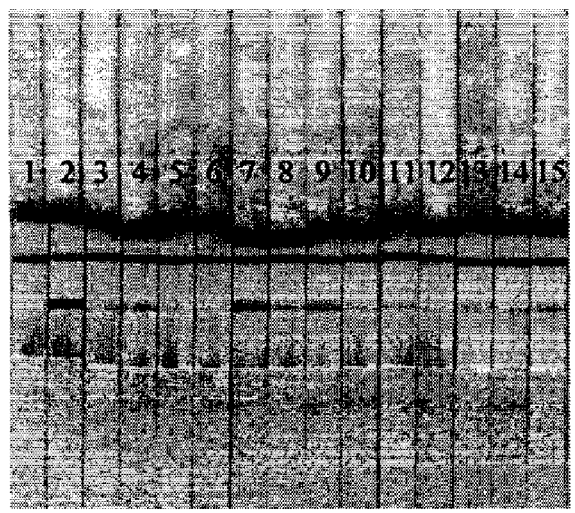

The results are shown in FIG. 3, wherein FIG. 3A represents the results obtained using gold colloid dried on a conjugate pad (the conventional lateral flow system), and FIG. 3B represents the results obtained using liquid gold colloid applied on the sample pad (the modified lateral flow system). The results indicate that the liquid gold system disclosed herein is highly superior to the conventional system. Lanes 1 in both FIGS. 3A and 3B represent negative sera, lanes 2 represent positive control serum, and lanes 3-6 represent a dilution panel prepared with a weakly positive serum. The conventional process could not detect antibodies in this panel. The modified lateral flow process (FIG. 3B) clearly detected the serum at all dilutions. Similarly, the rest of the lanes were used with different dilution panels prepared with different sera. The liquid gold formulation was clearly superior to the dried gold formulation in terms of signal strength.

Example 2

Detection of *Trypanosoma cruzi* (Chagas) Infection

In these studies, the *Trypanosoma cruzi* antigen ITC.8.2 (disclosed in International patent application no. WO 2007/056114) was employed in combination with dried gold in the conventional system and liquid gold formulation in the modified system. Various concentrations of liquid gold colloid, between 0.5 and 5 optical units, in a small volume were used. Following application of a small volume of sample (5 μl), a small volume of chase buffer, typically 20-80 μl was used to drive the reaction upward and immediately a small volume, typically 5-50 μl of liquid gold conjugate was added. Once the gold conjugate was absorbed into the test strip, another portion of chase buffer (50-500 μl) was added to help move the gold conjugate through the system. The results of this study are shown in FIGS. 4A-6B. Similar to the Kala-azar system described above, a dramatic improvement in sensitivity was observed using the modified system (results shown in FIGS. 4B, and 5B, compared to the conventional system (*T. cruzi* Detect Dipstick manufactured by InBios International, Inc., Seattle, Wash.; results shown in FIGS. 4A and 5A).

Figure 4A:
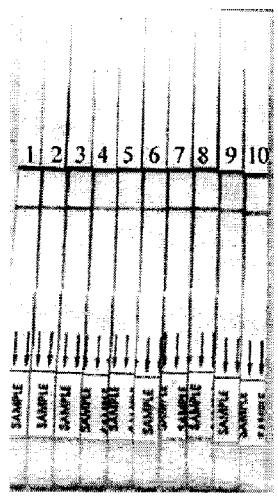
FIGS. 4A and 4B show the detection of antibodies to the *Trypanosoma cruzi* antigen ITC.8.2 using a conventional lateral flow system (FIG. 4A) and the modified lateral flow system disclosed herein (FIG. 4B), using ITC 8.2 applied at a concentration of 0.25 mg/ml.
Figure 4B:
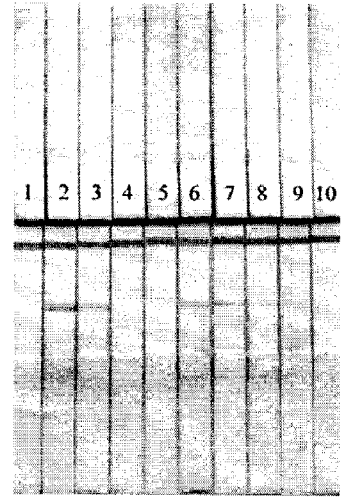

FIG. 4A represents the results obtained using gold colloid dried on a conjugate pad (the conventional lateral flow system), and FIG. 4B represents the results obtained using liquid gold colloid applied on the sample pad (the modified lateral flow system). Lane 1 represents negative control, lane 2 represents positive control and lane 3 represents weak positive control; lanes 4 and 5 represent normal human sera; lanes 6, 7 and 8 represent *T. cruzi* positive sera; and lanes 9 and 10 represent cross-reactive sera. The modified liquid gold system employed the antigen ITC8.2 sprayed at a concentration of 0.25 mg/ml on a Millipore Hi-Flow Plus membrane.

Figure 5A:
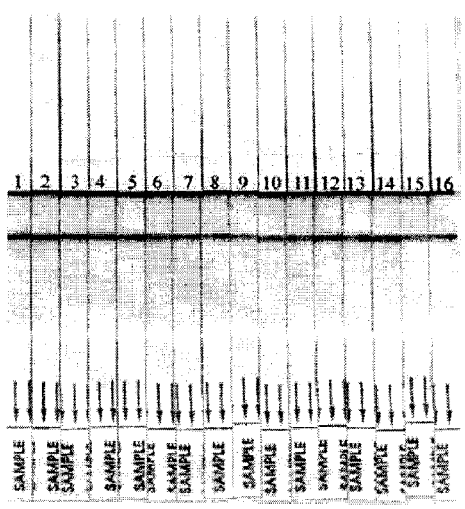
FIGS. 5A and 5B show a comparison of a conventional lateral flow system (FIG. 5A) and the modified lateral flow system disclosed herein (FIG. 5B), using normal human sera and the *T. cruzi* antigen ITC 8.2 applied at a concentration of 0.05 mg/ml.
Figure 5B:
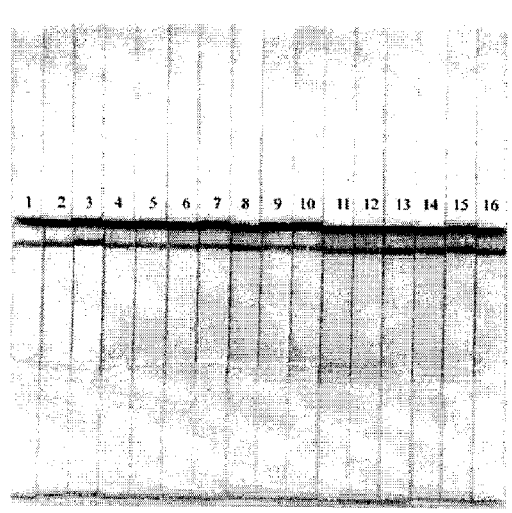

FIGS. 5A and 5B show the comparison between the modified liquid gold system (FIG. 5B) and the conventional dried gold system (FIG. 5A) with normal human sera. Antigen ITC8.2 was sprayed at a concentration of 0.05 mg/ml on Millipore Hi-Flow Plus membrane.

Figure 6A:
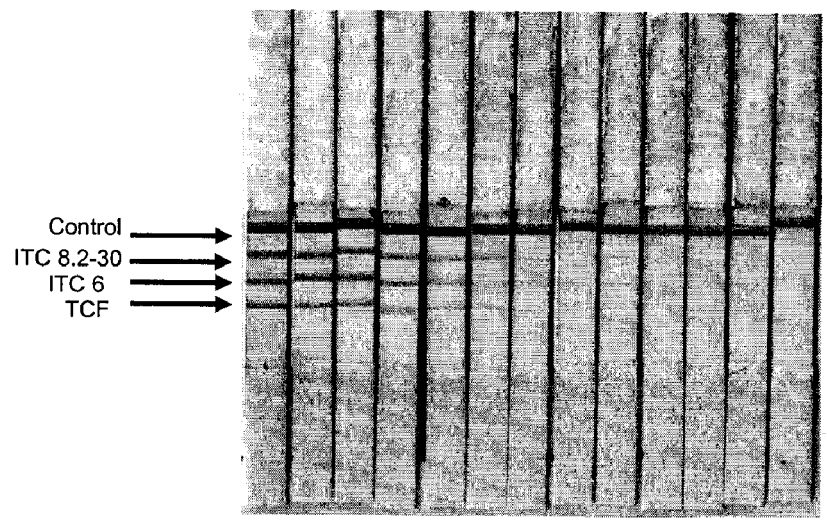
FIGS. 6A and 6B show the results of serial dilutions of a Chagas antibody-positive sample tested using the disclosed liquid gold system and the antigens ITC8.2-30, ITC6 and TCF.
Figure 6B:
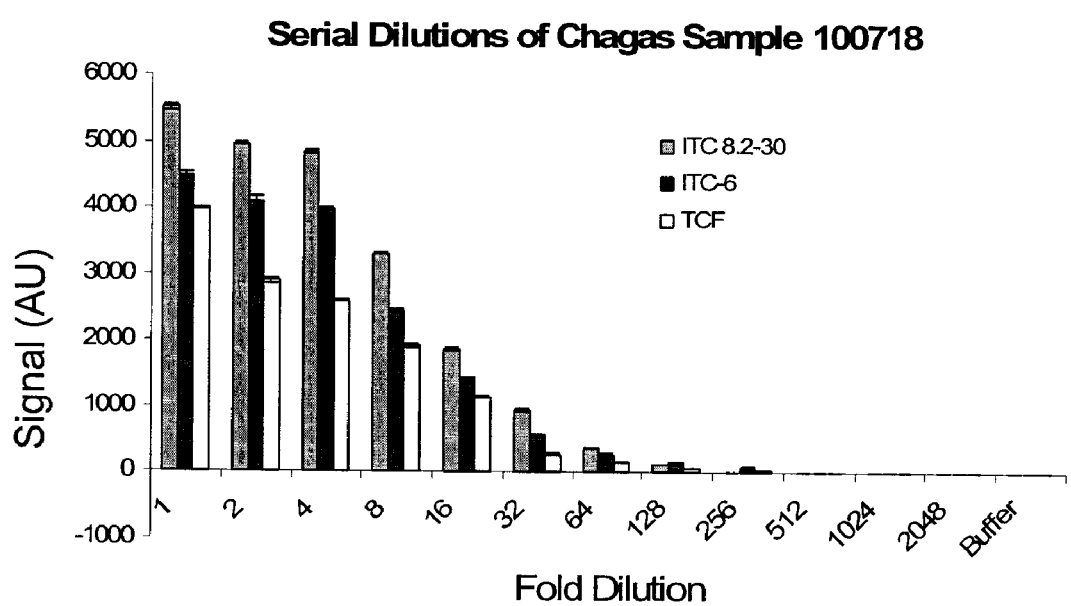

In further studies, serial dilutions of a Chagas antibody-positive sample were tested using the disclosed liquid gold system. Three antigens (ITC 8.2-30, ITC 6, and TCF) and a control line were sprayed onto the membrane to be tested. Quantifiable data was gathered by using a Unison Biotech strip reader. The results are shown in FIGS. 6A and B. The signal represents the average signal measured by the scanner from three repeated measurements of the same strip. Intra-assay variation was minimal and is represented by the error bars shown in FIG. 6B.

Figure 7A:
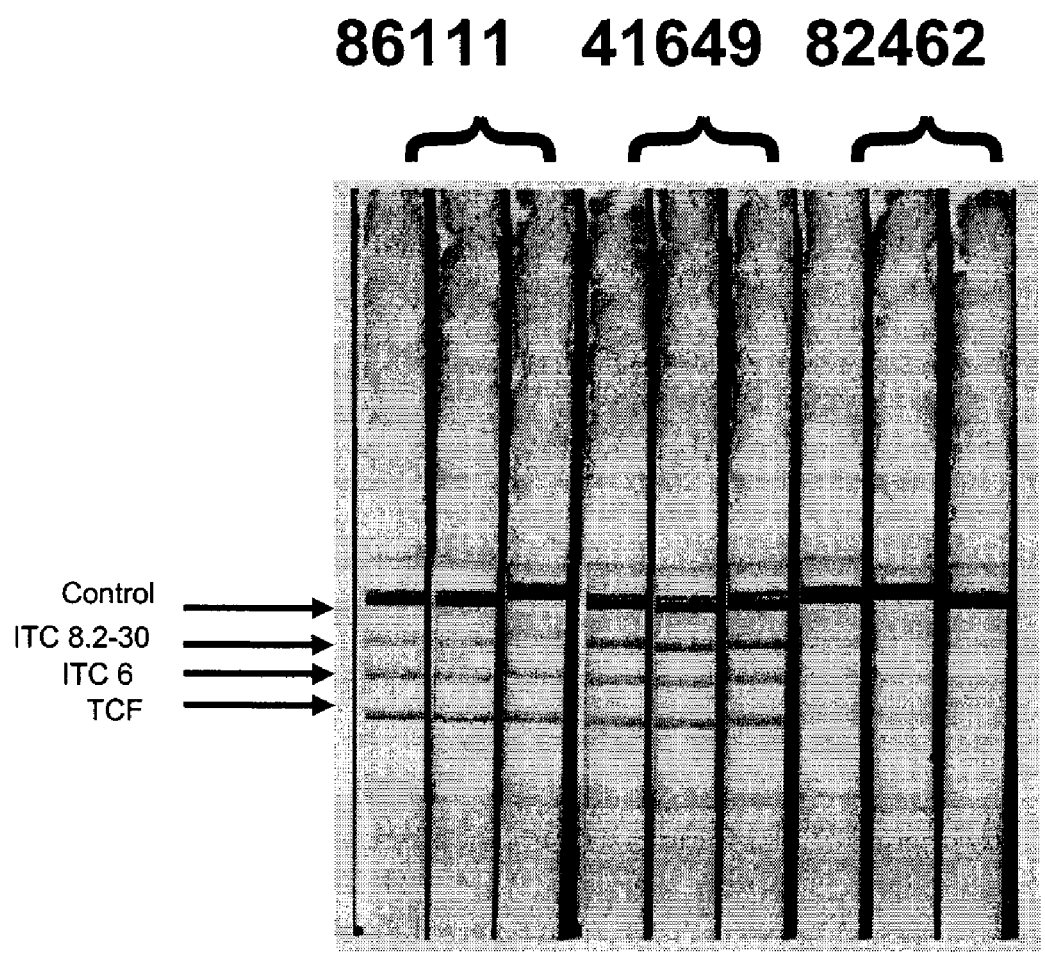
FIG. 7A shows the results of three Chagas seropositive samples tested using the disclosed liquid gold systems and the antigens ITC8.2-30, ITC6 and TCF.

FIG. 7A and Table 1 show the results from testing three Chagas seropositive samples in triplicate using the disclosed liquid gold system. Three antigens (ITC 8.2-30, ITC 6 and TCF) and a control line were sprayed onto the membrane. Visual inspection of the individual strips indicated little visible variation. However, by quantifying the intensity of the lines using the Unison Biotech scanner, the assay variation was readily quantified. As expected, the assay variation was greatest among samples that have a weaker observed reactivity.

TABLE 1

| Sample ID | ITC 8.2-30 + SUMO | ITC 6 | TCF |
| --- | --- | --- | --- |
| 86111 | 37.51% | 29.42% | 35.54% |
| 41649 | 11.22% | 12.40% | 12.93% |
| 82462 | 28.50% | 38.68% | 41.13% |

Example 3

Detection of Syphilis Infection

Cardiolipin is a phospholipid molecule which has been implicated in the diagnosis of syphilis (Pedersen et al., *J. Clin. Microbiol.* 25:1711-6, 1987). It has been shown that antibodies to cardiolipin exist in patients with active disease. Cardiolipin micelle was used to stripe test lines on a membrane as described. Similar to the above two systems, protein A gold conjugate was used for detection of antibodies in a dilution panel made with confirmed syphilis positive sera. The results (not shown), demonstrate that the gold conjugate in liquid formulation was more active than the dried gold formulation in the conventional system.

All references disclosed herein, including patent references and non-patent references, are hereby incorporated by reference in their entirety as if each was incorporated individually.

We claim:

1. A system for detecting a presence of a component of interest in a test sample, comprising:
   (a) a liquid formulation of an indicator conjugate including a first member of a binding pair, wherein the indicator conjugate is a gold conjugate; and
   (b) a lateral flow assay device, wherein the lateral flow assay device comprises:
      (i) a sample receiving region; and
      (ii) a capture membrane comprising a test region comprising an immobilized detection agent specific for the component of interest, and a control region comprising an immobilized second member of the binding pair, wherein the detection agent is selected from the group consisting of: *Leishmania* antigens, *T. cruzi* antigens, and cardiolipin micelle.

2. The system of claim 1, wherein the sample receiving region directly contacts the capture membrane.

3. The system of claim 1, wherein the lateral flow assay device lacks a conjugate pad.

4. The system of claim 1, wherein the lateral flow assay device further comprises a reservoir region positioned downstream of the capture membrane for absorbing an excess of fluid.

5. The system of claim 1, wherein the indicator conjugate is a protein A-gold conjugate.

6. A kit comprising the system of claim 1 and instructions for its use.

7. A method for detecting a presence of a component of interest in a liquid test sample, comprising the steps of:
   (a) providing a lateral flow assay device comprising:
      (i) a sample receiving region; and
      (ii) a capture membrane positioned downstream of the sample receiving region and comprising a test region including an immobilized detection agent specific for the component of interest and a control region including an immobilized control reagent, wherein the detection agent is selected from a group consisting of: *Leishmania* antigens, *T. cruzi* antigens, and cardiolipin micelle;
   (b) applying the test sample, a liquid formulation of an indicator conjugate and a first volume of a chase buffer to the sample receiving region, wherein the indicator conjugate is a gold conjugate; and
   (c) allowing a component-indicator conjugate complex to migrate through the capture membrane to the test region and contact the detection agent thereby immobilizing the component-indicator conjugate complex and forming a detectable signal,
wherein the presence of the component of interest in the test sample is indicated by the signal.

8. The method of claim 7, further comprising the step of applying a second volume of a chase buffer to the sample receiving region.

9. The method of claim 7, wherein the capture membrane directly contacts the test region.

10. The method of claim 7, wherein the lateral flow assay device lacks a conjugate pad.

11. The method of claim 7, wherein the lateral flow assay device further comprises a reservoir region positioned downstream of the capture membrane for absorbing an excess of fluid.

12. The method of claim 7, wherein the presence of the component of interest is indicative of the presence of an infectious disease.

13. The method of claim 12, wherein the infectious disease is selected from the group consisting of: leishmaniasis, Chagas disease and syphilis.

14. The method of claim 7, wherein the test sample is a biological sample.

15. The method of claim 14, wherein the biological sample is selected from the group consisting of: whole blood, serum, plasma, nasal secretions, sputum, urine, saliva, transdermal exudates, cerebrospinal fluid, vaginal secretions and urethral secretions.

16. The method of claim 7, wherein the indicator conjugate is a protein A-gold conjugate.

\* \* \* \* \*

UNITED STATES PATENT AND TRADEMARK OFFICE
CERTIFICATE OF CORRECTION

PATENT NO.        : 8,399,261 B2
APPLICATION NO.   : 12/666637
DATED             : March 19, 2013
INVENTOR(S)       : Mazbahul Kabir et al.

Page 1 of 1

It is certified that error appears in the above-identified patent and that said Letters Patent is hereby corrected as shown below:

| Col. No. | Line(s) | Edits |
|----------|---------|-------|
| 9 | 14 | Replace "conjugate including" with --conjugate comprising-- |

Signed and Sealed this
Ninth Day of July, 2013

Teresa Stanek Rea
*Acting Director of the United States Patent and Trademark Office*